United States Patent [19]

Turro et al.

[11] Patent Number: 4,971,664

[45] Date of Patent: Nov. 20, 1990

[54] TERMINAL CHLORINATION OF NORMAL ALKANE HYDROCARBONS

[75] Inventors: Nicholas J. Turro, Tenafly, N.J.; James R. Fehlner, Moscow, Pa.

[73] Assignee: Inrad, Inc., Northvale, N.J.

[21] Appl. No.: 218,215

[22] Filed: Jul. 13, 1988

[51] Int. Cl.$^5$ .............................................. C07C 17/00
[52] U.S. Cl. .............................. 204/158.12; 204/59 R; 570/196
[58] Field of Search ....................... 204/158.12, 59 R; 570/196, 254

[56] References Cited

U.S. PATENT DOCUMENTS 2,998,459  8/1961  Baker .................................. 570/207
3,951,770  4/1976  McCoy et al. ....................... 204/163

OTHER PUBLICATIONS

Jacobs, P. A. "Properties of the End Members in the Pentasil—Family of Zeolites: Characterization as Adsorbents," *Zeolites*, pp. 161–168, vol. 1, (1981).

Richards, R. E. "Sorption and Packing of n-Alkane Molecules in ZSM-5," *Langmuir*, pp. 335–340, vol. 3, (1987).

Perry, Eli; "Directing a Chlorination Reaction", *J. Org. Chem.*, (1970), vol. 35, No. 6, pp. 2053–2054.

Jacobs, Peter A. et al.; "Properties of the End Members in the Pentasil-Family of Zeolites: Characterization as Adsorbents", *Zeolites*, (1981), vol. 1, pp. 161–168.

Olson, D. H. et al.; "Crystal Structure and Structure-Related Properties of ZSM-5", *J. Phys. Chem.* (1981), vol. 85, pp. 2238–2243.

Richards, Robin E. et al.; "Sorption and Packing of n-Alkane Molecules in ZSM-5", *Langmuir*, (1987), vol. 3, pp. 335–340.

von Ballmoos, R. et al.; "Zoned Aluminum Distribution in Synthetic Zeolite ZSM-5", *Nature*, (1981), vol. 289, pp. 782–783.

Herron, Norman et al.; "A Highly Selective Zeolite Catalyst for Hydrocarbon Oxidation. A Completely Inorganic Mimic of the Alkane $\omega$-Hydroxylases", *J. Am. Chem. Soc.*, (1987), vol. 109, pp. 2837–2839.

Herron, N. et al.; "Selective Catalytic Oxygenation of Hydrocarbons with Molecular Oxygen at Room Temperature—a Completely Inorganic Mimic of Monoxygenase Enzymes," Preprint, *Symposium on Advances in Oil Shale Technology*, vol. 32, No. 1, (1987), pp. 200–204.

*Primary Examiner*—John F. Niebling
*Assistant Examiner*—Isabelle R. McAndrews
*Attorney, Agent, or Firm*—Shapiro and Shapiro

[57] ABSTRACT

A terminally chlorinated normal alkane hydrocarbon is produced at high terminal selectivity, by adsorbing a normal alkane into a select zeolite and chlorinating the adsorbed alkane in the zeolite. The zeolite may be of a type having internal channels of diameter slightly larger than that of the alkane, and substantially no internal chambers, and may be selected from the pentasil family of zeolites. The chlorination reaction may be conducted under heating to enhance terminal selectivity even further, in many cases to levels approaching 100%.

26 Claims, No Drawings

4,971,664

TERMINAL CHLORINATION OF NORMAL ALKANE HYDROCARBONS

BACKGROUND OF THE INVENTION

This invention relates to chemical processing of normal (straight chain) alkane hydrocarbons and is more particularly concerned with a method of producing chlorinated normal alkanes at high terminal selectivity.

Terminally chlorinated normal alkanes, also known as primary chloroalkanes, are especially useful ingredients for the synthesis of numerous organic compounds. Such compounds include various fatty acids, amines, alcohols, esters, and sulfonates—which are in turn useful in the preparation of a wide range of commercial products.

As is well known, primary chloroalkanes are readily produced by direct reaction of normal alkane hydrocarbons with chlorinating agents, such as chlorine gas. The replacement of hydrogen of the alkane with chlorine may be facilitated by the presence of a reaction initiating agent such as light (photo initiation), heat (thermal initiation), or a catalyst such as a peroxy compound (chemical initiation). Such reactions are generally not used in the preparation of primary chloroalkanes in pure form, however, because they produce not only the terminally substituted species, but a mixture of reaction products from which the primary product must be separated. To compound the problem, these reactions substantially favor the formation of secondary chloroalkanes—that is, chlorination of interior carbons of the alkane chain rather than of the terminal carbons. The higher selectivity for secondary chlorination is due to the greater number of secondary hydrogens (in long chain alkanes) and their greater reactivity in comparison to the terminal or primary hydrogens. Chlorination of a normal alkane thus generally results in a relatively large proportion of secondary product and only a small proportion of primary product. While the two products can be separated, the yield of primary product is ordinarily too small to justify the effort. Accordingly, the art has been forced to use other techniques of producing primary chloroalkanes.

In an effort to make direct chlorination a commercially feasible alternative for primary chloroalkane preparation, researchers have sought ways to control the reaction in such a manner as to increase terminal selectivity. Terminal selectivity is commonly defined in either of two ways: as the weight percent of terminally chlorinated product in the total monochlorinated products produced by the reaction (denoted herein as "$S_t$"), or as the probability of reaction of a primary hydrogen versus a secondary hydrogen for the monochlorinated products (denoted herein by "$S_o$").

Ideally speaking, a controlled reaction should maximize not only terminal selectivity, but also conversion and selectivity for monochlorination. Conversion is defined as the weight percent of alkane consumed in the chlorination reaction. Selectivity for monochlorination (denoted herein by "$S_m$") is defined as the weight percent of monochlorinated product in the total chlorination products. Thus, for a given terminal selectivity, it will be apparent that the higher the conversion and selectivity for monochlorination, the higher will be the yield of primary product.

One proposed technique for increasing terminal selectivity of the chlorination reaction involves preadsorption of the alkane with a particulate adsorbent. In an article entitled "Directing a Chlorination Reaction," which appeared in the Journal of Organic Chemistry, Vol. 35, No. 6, 1970 (pages 2053–2054), Eli Perry reported that increased selectivity for 1-chlorohexane could be obtained by chlorinating normal hexane adsorbed into an X type zeolite. X type zeolites are low silica zeolites (silicon-to-aluminum ratio around 2–3 by weight) characterized internally by a network of chambers interconnected by channels. Perry's best values for $S_t$ (about 50%) and $S_o$ (about 3) held for conversions of only about 1%. At 2% conversion, terminal selectivity dropped significantly; and at commercially practical conversion levels, terminal selectivity was not much better than for neat reactions ($S_o$ about 0.4, $S_t$ about 15%). Perry was unable to attain good product recovery levels with channel sizes less than 10 angstroms.

In U.S. Pat. No. 3,951,770, David McCoy reported improved terminal selectivities at higher conversions with non-zeolitic (non-porous) adsorbents. McCoy achieved terminal selectivities as high as about $S_t = 27\%$, $S_o = 1.2$ for 1-chlorododecane, but results ranged more typically around $S_t = 15\%$–20%, $S_o = 0.6$–0.8, depending on the adsorbent. As a basis for comparison, McCoy ran tests with certain A type and mordenite zeolites. These zeolites failed to give any appreciable improvement over neat (no adsorbent) chlorination. As will be of apparent significance later herein, the A type zeolites have a similar internal structure to the X type zeolites and a slightly lower silicon-to-aluminum ratio (about 1 by weight); and the mordenites have a unidirectional internal channel network with no chambers.

SUMMARY OF THE INVENTION

The present invention is also based on the use of an adsorbent to control terminal selectivity of the chlorination reaction. However, as will be seen hereinafter, the invention achieves terminal selectivities far beyond those heretofore reported. The invention is especially surprising when considered in view of the teachings of McCoy and Perry because it involves the use of a zeolite adsorbent with channel sizes less than 10 angstroms.

More particularly, in accordance with one of its principal aspects, the invention provides a method of producing a terminally chlorinated normal alkane at high terminal selectivity, which comprises adsorbing a normal alkane into a pentasil zeolite, and chlorinating the adsorbed alkane in the zeolite.

While the invention is not to be limited by theory, we believe that the superior terminal selectivities achieved by the foregoing method are attributable to certain internal structural features exhibited by the pentasil zeolites. The pentasil zeolites constitute a family of high silica zeolites (silicon-to-aluminum ratios typically from about 15 to over 1,200 by weight) which are made up of so-called pentasil crystallites. "Pentasil" refers to the pentagonal silicon cells which constitute the building blocks of the zeolite crystal structure. The pentasil zeolites are characterized internally by a network of perpendicular intersecting channels, with no chambers being present. At one end of the pentasil family, the channels are all straight, this zeolite being commonly designated ZSM-11. At the other end of the family, the channels extending in one direction are straight and the intersecting channels are sinusoidal, this zeolite commonly being designated ZSM-5. The sinusoidal channels are nearly circular and have a diameter of about 5.5 angstroms, whereas the straight channels are slightly elliptical, with major and minor diameters of about 5.5 and 5.1 angstroms, respectively.

Notably, the aforementioned channel diameters are only slightly larger than the molecular diameters of normal alkanes, which run about 4.3 angstroms. We believe that this factor is key to the success of the present invention. More particularly, in a simple manner of speaking, we believe that the channels hold adsorbed alkane molecules lengthwise such that it is primarily the terminal hydrogens which are exposed to attack by chlorine. This would appear to explain the poor terminal selectivities exhibited by mordenites and X and A type zeolite adsorbents. Mordenites, for example, have unidirectional internal channels as indicated earlier, but the channel diameter runs about 7 angstroms. This diameter would probably be sufficient for chlorine to bypass the terminal hydrogens of an adsorbed alkane molecule and to attack secondary positions. X and A type zeolites have relatively large internal chambers connected by smaller channels. An alkane molecule in a large chamber would probably have difficulty threading its way into a small channel, so that alkane adsorption and recovery would be difficult, as appears to be borne out by Perry's work.

Thus, according to another of its principal aspects, the invention provides a method of producing a terminally chlorinated normal alkane at high terminal selectivity, which comprises adsorbing a normal alkane into a zeolite of a type having internal channels of diameter slightly larger than the molecular diameter of the alkane (and preferably from about 5 to about 6 angstroms in diameter), with no internal chambers, and chlorinating the adsorbed alkane in the zeolite.

As will be seen hereinafter, the invention not only achieves high terminal selectivities at low conversions, but also at high conversions. Indeed, terminal selectivity tends to increase with conversion in the practice of the invention. Thus, the invention is well suited to commercial needs. Quite unexpectedly, and in contrast to Perry's experience, we have also found that when the method of the invention is conducted with heating, terminal selectivities are even further increased. In many cases, secondary product is virtually eliminated and terminal selectivity approaches $S_t = 100\%$, $S_o = \infty$.

The invention will now be explained in detail, and its various features and advantages will become more apparent from the ensuing description.

DETAILED DESCRIPTION OF THE INVENTION

It is preferred that the normal alkanes to be treated in the practice of the invention be in either solid or liquid phase at processing temperatures—usually from room temperature to around 75° C. Although it is within the broader principles of the invention to use alkanes in gaseous form as starting materials, such as is disclosed in the aforementioned article by Perry, alkanes in solid or liquid phase are readily adsorbed into and desorbed from the zeolites by the use of suitable solvents. Accordingly, alkanes having chain lengths of at least 9 carbon atoms are preferred. The maximum preferred chain length is 20 carbon atoms. However, the invention may be advantageously applied to normal alkanes having more than 20 carbon atoms if adsorption and desorption times are not a prime consideration. (A longer molecule requires more time to pass into and out of the zeolite channels than a shorter molecule). Thus, the preferred alkanes for practice of the invention are:

n-nonane
n-decane
n-undecane
n-dodecane
n-tridecane
n-tetradecane
n-pentadecane
n-hexadecane
n-heptadecane
n-octadecane
n-nonadecane
n-eicosane As will be seen in the later-appearing specific examples, the starting alkane need not be in pure hydrocarbon form, but may be substituted—usually at the 1-position. Illustrative substituents include:

Chlorine
Bromine
Nitrile
Aldehyde

When chlorinated in accordance with the invention, the substituted alkanes are converted to disubstituted alkanes with high selectivity for the unsubstituted terminal position (i.e., the $\omega$ position). Like the 1-chloroalkanes, the terminally disubstituted alkanes may be used as chemical intermediates in various organic synthesis procedures. For example, $\omega$-chloronitriles may be converted to amino acids by displacement of the chlorine with ammonia and hydrolysis of the nitrile group to the acid. They may also be converted to amino alcohols by displacement of the chlorine with hydroxide and reduction of the nitrile group to the amine. As another example, $\alpha,\omega$-dichloroalkanes may be converted to dihydroxyalcohols by displacement of the chlorines with hydroxide, or to diamines by displacement of the chlorines with ammonia. Techniques for accomplishing the various reactions just mentioned are well known to those skilled in the art.

Among the pentasil family of zeolites, ZSM-5 is the most preferred for the practice of the invention. As will be apparent from the specific examples given later, the ZSM-5 end of the pentasil family tends to provide better terminal selectivities than the ZSM-11 end under comparable reaction conditions. A most notable advantage of the pentasil zeolites in general is that they are essentially inert to the components used in and produced by the chlorination reaction (chlorine, hydrochloric acid, etc.) Thus, they may be used repeatedly. Specific zeolites found useful in the practice of the invention include zeolites manufactured by Union Carbide under designations LZ-105-5 and S-115 (also called "silicalite").

As indicated earlier, the pentasil zeolites are available in a wide range of silicon-to-aluminum ratios—from about 15 to over 1,200 by weight. For a given pentasil family member, lower silicon-to-aluminum ratios result in higher terminal selectivities for comparable reaction conditions. Thus, low silicon-to-aluminum ratios, say about 70 or less, are preferred for the purposes of the invention, a ratio of 28 or less being most preferred.

Various adsorption techniques may be used in practice of the invention. The preferred alkanes, both unsubstituted and substituted, are easily adsorbed by adding the alkane dissolved in a suitable solvent (such as pentane or methylene chloride) to a weighed sample of the zeolite adsorbent. After allowing sufficient time for adsorption of the alkane (e.g., 24 hours), the solvent may be evaporated, leaving the zeolite and adsorbed alkane charge.

The degree to which the zeolite is loaded with alkane has a significant effect on the results of the chlorination reaction. Loading is defined as the weight of adsorbed alkane as a percentage of the weight of zeolite adsorbent. Optimum loading depends on whether the zeolite is "wet" or predried. Predrying allows for higher loadings while maintaining high terminal selectivity. For wet zeolites, the optimum loading range is from about 0.5% to about 2%, with 2% being most preferred. For dry zeolites, the optimum loading range is from about 0.5% to about 8%, with best results usually being obtained at around 6% loading. At loadings above these ranges, terminal selectivity tends to drop to lower values. It has been determined that this phenomenon results from adsorption of excess alkane on the outer surface of the zeolite, as opposed to inside. Excess alkane may be removed prior to the chlorination reaction by washing the heavily loaded zeolite with a solvent having molecules too large to enter the zeolite channels. Iso-octane is effective for this purpose. Loadings below the aforementioned ranges may be too small to be practical for some applications.

The chlorination reaction is preferably carried out by exposing the zeolite and adsorbed alkane charge to a chlorination agent, which is preferably chlorine gas, in the presence of a reaction initiating agent. Depending on the reaction environment, chlorine will normally be added to the charged zeolite at a ratio of about 0.2 to about 500 moles per mole of alkane, and in either pure form (100% concentration) or diluted in an inert gas such as argon or nitrogen to as low as about 0.1% concentration.

With small samples of charged zeolite, say of the order of a few milligrams, the reaction is readily conducted by exposing an agitated bed of the charged zeolite to the chlorine gas. However, with larger samples, the reaction is preferably carried out in a fluidized bed of the charged zeolite. Chlorine gas may be introduced into the bed with an inert fluidizing gas (e.g., argon or nitrogen). Safety considerations will normally dictate the use of a low concentration of chlorine in the fluidizing gas, say of the order of a few percent or less. Of course, fluidization of the bed ensures thorough mixing of the sample so that large chlorination ratios are generally unnecessary. The fluidized bed examples appearing hereinafter, for instance, by and large used chlorination ratios well below 40 moles per mole of charge alkane.

Among the earlier mentioned reaction initiating agents, light is the most preferred. Visible and ultraviolet wavelengths are both effective, but ultraviolet wavelengths tend to produce better results. Specifically, the preferred wavelengths range from about 2,000 to about 7,000 angstroms, with 2,000-4,000 angstroms being the most preferred part of the range.

A surprising and highly important aspect of the invention is the influence of reaction temperature on terminal selectivity. Variations in temperature from $-25°$ C. to $25°$ C. generally have little effect on the degree of improvement in terminal selectivity attained by the invention. However, when reaction temperature is increased to around the $40°$ C.–$75°$ C. range, terminal selectivity increases even more dramatically—in some cases to as much as $S_t = 100\%$, $S_o = \infty$. Such high terminal selectivities lead to increased yields and simplify recovery of the desired product.

The terminally chlorinated products are readily recovered from the zeolite by conventional techniques. For example, the reaction products (as well as any unreacted product) may be desorbed from the zeolite by extraction with solvents such as methylene chloride. After evaporation of the solvent, the recovered products may be subjected to distillation to separate the terminally chlorinated product from secondary product and unreacted alkane.

SPECIFIC EXAMPLES

The following examples demonstrate the superior terminal selectivity characteristics of the invention. In each case, an appropriate aliquot of normal alkane (either unsubstituted or substituted) dissolved in pentane was added to the zeolite adsorbent (finely powdered) to achieve the desired loading. The resulting slurry was allowed to stand at room temperature for at least 24 hours, and the pentane was then evaporated (under reduced pressure for "wet" zeolite samples and in a desiccator for predried zeolite samples). All examples were run with "wet" zeolites, except as otherwise indicated.

The chlorination step was conducted using one of two techniques, depending on the sample size. Small samples (10 mg total zeolite and adsorbed alkane) were placed in a quartz reactor and purged with argon, or in the case of chlorination with pure chlorine, purged directly with chlorine. A measured amount of chlorine was then added to the reactor, and the reactor was sealed. The samples were rotated under an ultraviolet lamp (BHK Model No. 88-9102-02) for a predetermined time.

For larger samples (about 200 mg total zeolite adsorbed alkane), the zeolite was fluidized with dry oxygen-free nitrogen, and the chlorine was introduced into the fluidizing gas stream at a predetermined rate while the reactor was irradiated with the ultraviolet lamp. Both large and small samples were chlorinated at atmospheric pressure and, unless otherwise indicated, at room temperature ($25°$ C.).

After completion of the reaction, the sample was purged with argon (small samples) or nitrogen (fluidized bed runs), and reaction products were recovered by desorption with methylene chloride. The zeolite was then removed by filtration and thoroughly rinsed with methylene chloride. The methylene chloride rinse was combined with the desorption solvent to maximize recovery. The collected solvent was then evaporated and replaced with hexane. The resulting solution was analyzed by gas chromatography.

Tables I and II show the results of examples of the invention as applied to normal alkanes (unsubstituted) of various chain lengths. Sample sizes were 10 mg. The tables indicate chain lengths by number of carbon atoms (e.g., $C_9$ for n-nonane) and show the loading and reaction time ("Exposure") for each example and the resulting conversion ("Conv."), selectivity for monochlorination ($S_m$), and terminal selectivity ($S_t$ and $S_o$). Examples 1–27 were conducted with a ZSM-5 zeolite (Na ZSM-5, Si/Al=24), and Examples 28–40 were conducted with a ZSM-11 zeolite (Na ZSM-11, Si/Al=28).

TABLE I

| Chain Length | Ex.* | Load (%) | Exposure (minutes) | Conv. (%) | $S_m$ (%) | $S_t$ (%) | $S_o$ |
|---|---|---|---|---|---|---|---|
| $C_9$ | 1 | .5 | 5 | 67 | 51 | 70 | 5.6 |
|  | 2 | 2 | .5 | 7 | 54 | 53 | 2.6 |

TABLE I-continued

| Chain Length | Ex.* | Load (%) | Exposure (minutes) | Conv. (%) | $S_m$ (%) | $S_t$ (%) | $S_o$ |
|---|---|---|---|---|---|---|---|
|  | 3 | 2 | 5 | 33 | 65 | 62 | 3.8 |
|  | 4 | 2 | 5 | 75 | 36 | 54 | 2.7 |
|  | 5 | 8 | 5 | 26 | 75 | 57 | 3.1 |
|  | 6 | 30 | 5 | 26 | 54 | 29 | 0.9 |
| $C_{12}$ | 7 | .5 | 10 | 40 | 33 | 63 | 5.7 |
|  | 8 | 1 | 10 | 51 | 57 | 60 | 5.0 |
|  | 9 | 2 | 10 | 35 | 48 | 64 | 5.9 |
|  | 10 | 2 | 10 | 45 | 53 | 66 | 6.5 |
|  | 11 | 3 | 10 | 36 | 56 | 51 | 3.5 |
|  | 12 | 4.5 | 10 | 34 | 62 | 41 | 2.3 |
|  | 13 | 6 | 10 | 32 | 56 | 35 | 1.8 |
|  | 14 | 10 | 10 | 32 | 63 | 30 | 1.4 |
|  | 15 | 20 | 10 | 36 | 78 | 26 | 1.2 |
|  | 16 | 30 | 10 | 33 | 70 | 31 | 1.5 |
|  | 17 | 40 | 10 | 26 | 73 | 34 | 1.7 |
|  | 18 | 50 | 10 | 32 | 84 | 35 | 1.8 |
| $C_{13}$ | 19 | 2 | 10 | 53 | 39 | 59 | 5.3 |
|  | 20 | 2 | 10 | 48 | 38 | 52 | 4.0 |
| $C_{18}$ | 21 | 2 | 10 | 17 | 59 | 65 | 10 |
|  | 22 | 2 | 30 | 24 | 50 | 61 | 8.3 |
| $C_{20}$ | 23 | .5 | 10 | 37 | 42 | 61 | 9.2 |
|  | 24 | 2 | 10 | 21 | 67 | 67 | 12 |
|  | 25 | 2 | 30 | 44 | 24 | 59 | 8.6 |
|  | 26 | 8 | 10 | 13 | 47 | 15 | 1.0 |
|  | 27 | 30 | 10 | 18 | 50 | 6 | 0.4 |

*Examples 7-9, 11-18, 20, and 22 chlorinated with pure chlorine (15 ml). All others chlorinated with 0.1 ml chlorine in argon (concentration 0.7% Cl).

TABLE II

| Chain Length | Ex.* | Load (%) | Exposure (minutes) | Conv. (%) | $S_m$ (%) | $S_t$ (%) | $S_o$ |
|---|---|---|---|---|---|---|---|
| $C_9$ | 28 | 2 | .03 | 8 | 47 | 44 | 1.8 |
|  | 29 | 2 | .2 | 29 | 48 | 49 | 2.2 |
|  | 30 | 2 | .5 | 91 | 23 | 59 | 3.3 |
| $C_{12}$ | 31 | 2 | .05 | 10 | 78 | 49 | 3.2 |
|  | 32 | 2 | .5 | 32 | 60 | 47 | 3.0 |
|  | 33 | 2 | 2 | 36 | 71 | 47 | 3.0 |
|  | 34 | 2 | 10 | 52 | 64 | 44 | 2.6 |
|  | 35 | 2 | 140 | 71 | 48 | 48 | 3.1 |
| $C_{20}$ | 36 | 2 | .5 | 16 | 43 | 48 | 5.4 |
|  | 37 | 2 | 3 | 31 | 63 | 52 | 6.4 |
|  | 38 | 2 | 10 | 60 | 64 | 38 | 3.6 |
|  | 39 | 2 | 240 | 51 | 43 | 40 | 3.9 |
|  | 40 | 2 | 1135 | 62 | 42 | 36 | 3.3 |

*All examples chlorinated with 0.1 ml chlorine in argon (concentration 0.7% Cl).

Examples 41-47, summarized in Table III, show how predrying of the zeolite affects the relationship between loading and terminal selectivity. These examples were run with various loadings of dodecane on ZSM-5 zeolite (Na ZSM-5, Si/Al=24) which was dried to constant weight in a 500° C. oven prior to adsorption of the alkane. 10 mg samples were chlorinated with 0.1 ml of chlorine (0.7% in argon) for 10 minutes. Whereas optimum loading for wet zeolites is from about 0.5% to about 2% (see, for example, Table I), Table III shows that for predried zeolites, higher terminal selectivities are maintained even at 8% loading.

TABLE III

| Ex. | Load (%) | Conv. (%) | $S_m$ (%) | $S_t$ (%) | $S_o$ |
|---|---|---|---|---|---|
| 41 | 2 | 42 | 55 | 57 | 4.4 |
| 42 | 6 | 10 | 86 | 66 | 6.5 |
| 43 | 8 | 11 | 84 | 62 | 5.4 |
| 44 | 10 | 10 | 48 | 45 | 2.7 |
| 45 | 12 | 6 | 88 | 45 | 2.7 |
| 46 | 2 | 42 | 23 | 57 | 4.4 |

TABLE III-continued

| Ex. | Load (%) | Conv. (%) | $S_m$ (%) | $S_t$ (%) | $S_o$ |
|---|---|---|---|---|---|
| 47 | 6 | 11 | 75 | 62 | 5.4 |

Examples 48-81 show the effects of temperature on terminal selectivity. Examples 48-71, summarized in Table IV, were run using 200 mg samples at 2% loading of dodecane on wet ZSM-5 (Na ZSM-5, Si/Al=24). The zeolite bed was fluidized with nitrogen gas, as indicated earlier, and chlorine gas was introduced into the bed with the fluidizing nitrogen at a flow rate of 0.5 ml/min for a concentration of 0.1% chlorine. Bed temperature was controlled by heating or cooling the fluidizing gas as necessary. Examples 72-81, summarized in Table V, were conducted in the same fashion, except that eicosane was used in place of dodecane.

TABLE IV

| Temp. (°C.) | Ex. | Exposure (minutes) | Conv. (%) | $S_m$ (%) | $S_t$ (%) | $S_o$ |
|---|---|---|---|---|---|---|
| −25 | 48 | .25 | 9 | 83 | 61 | 5.2 |
|  | 49 | .5 | 10 | 77 | 64 | 5.9 |
|  | 50 | 1 | 12 | 73 | 62 | 5.4 |
|  | 51 | 2 | 15 | 68 | 63 | 5.7 |
|  | 52 | 5 | 20 | 72 | 62 | 5.4 |
|  | 53 | 15 | 32 | 60 | 60 | 5.0 |
|  | 54 | 30 | 72 | 57 | 64 | 5.9 |
| 25 | 55 | .25 | 14 | 75 | 61 | 5.2 |
|  | 56 | 1 | 5 | 80 | 53 | 3.8 |
|  | 57 | 2 | 10 | 78 | 63 | 5.7 |
|  | 58 | 3 | 10 | 71 | 64 | 5.9 |
|  | 59 | 5 | 15 | 58 | 66 | 6.5 |
|  | 60* | 5 | 6 | 76 | 53 | 3.8 |
|  | 61 | 15 | 22 | 48 | 71 | 8.2 |
| 40 | 62 | 5 | 14 | 65 | 98 | 160 |
|  | 63* | 5 | 5 | 65 | 79 | 13 |
| 50 | 64 | 5 | 34 | 71 | 100 | ∞ |
|  | 65* | 5 | 6 | 70 | 72 | 8.6 |
| 60 | 66 | 5 | 22 | 72 | 100 | ∞ |
|  | 67* | 5 | 14 | 62 | 99 | 330 |
| 75 | 68 | 1 | 5 | 63 | 100 | ∞ |
|  | 69 | 3 | 19 | 74 | 100 | ∞ |
|  | 70 | 5 | 32 | 66 | 100 | ∞ |
|  | 71 | 15 | 82 | 39 | 100 | ∞ |

*UV lamp off; low level ambient light only.

TABLE V

| Temp. (°C.) | Ex. | Exposure (minutes) | Conv. (%) | $S_m$ (%) | $S_t$ (%) | $S_o$ |
|---|---|---|---|---|---|---|
| 25 | 72 | .25 | 2.5 | 64 | 59 | 8.5 |
|  | 73 | 1 | 3 | 65 | 62 | 9.6 |
|  | 74 | 3 | 6 | 62 | 59 | 8.5 |
|  | 75 | 10 | 14 | 71 | 68 | 13 |
|  | 76 | 30 | 17 | 48 | 84 | 31 |
|  | 77 | 60 | 22 | 50 | 90 | 53 |
| 75 | 78 | .25 | 10 | 69 | 98 | 290 |
|  | 79 | 3 | 7 | 51 | 100 | ∞ |
|  | 80 | 10 | 10 | 64 | 100 | ∞ |
|  | 81 | 30* | 23 | 0 | — | — |

*Exposure time at indicated temperature may have been sufficient to cause desorption and loss of alkane and/or to initiate further reactions of monochlorinated products.

Examples 82-94, summarized in Table VI, demonstrate the effect of silicon-to-aluminum ratio on terminal selectivity. These examples were run in the same manner as Examples 48-71 (2% dodecane loading on ZSM-5 zeolite, etc.), except that zeolite in Examples 86-90 had a silicon-to-aluminum ratio of 70 and the zeolite in Examples 91-94 had a ratio of 1,220—this zeolite commonly being known as "silicalite."

TABLE VI

| Ex. | Si/Al | Exposure (minutes) | Temp. (°C.) | Conv. (%) | $S_m$ (%) | $S_t$ (%) | $S_o$ |
|---|---|---|---|---|---|---|---|
| 82 | 24 | 1 | 25 | 13 | 54 | 93 | 38 |
| 83 |  | 5 | 25 | 20 | 55 | 82 | 15 |
| 84 |  | 5 | 40 | 29 | 55 | 98 | 130 |
| 85 |  | 1 | 55 | 19 | 74 | 100 | ∞ |
| 86 | 70 | 1 | 25 | 6 | 50 | 62 | 5 |
| 87 |  | 5 | 25 | 8 | 38 | 57 | 4 |
| 88 |  | 5 | 55 | 33 | 39 | 100 | ∞ |
| 89* |  | 5 | 55 | 12 | 33 | 94 | 56 |
| 90* |  | 10 | 25 | 2 | 0 | — | — |
| 91 | 1220 | 1 | 25 | 22 | 55 | 47 | 3 |
| 92 |  | 5 | 35 | 35 | 51 | 47 | 3 |
| 93 |  | 5 | 40 | 28 | 28 | 75 | 10 |
| 94 |  | 5 | 55 | 11 | 73 | 97 | 130 |

*UV lamp off; low level ambient light only.

Tables VII and VIII summarize the results of additional examples which demonstrate the effect of predrying on the relationship between loading and terminal selectivity—in particular, with zeolites of higher silicon-to-aluminum ratios than that of the predried zeolite in the earlier examples of Table III.

All examples used 10 mg of ZSM-5 zeolite charged with dodecane. Table VII shows the results for examples run with "wet" zeolite, and Table VIII shows the results for examples run with predried zeolite.

TABLE VII

| Ex.* | Si/Al | Load (%) | Conv. (%) | $S_m$ (%) | $S_t$ (%) | $S_o$ |
|---|---|---|---|---|---|---|
| 95 | 70 | .5 | 28 | 54 | 43 | 2.5 |
| 96 |  | 2 | 32 | 69 | 44 | 2.6 |
| 97 |  | 3 | 37 | 62 | 46 | 2.8 |
| 98 |  | 10 | 7 | 71 | 19 | 0.8 |
| 99 |  | 20 | 18 | 78 | 15 | 0.6 |
| 100 |  | 40 | 33 | 42 | 20 | 0.8 |
| 101 | 1220 | .5 | 36 | 64 | 37 | 2.0 |
| 102 |  | 2 | 6 | 47 | 35 | 1.8 |
| 103 |  | 4 | 27 | 74 | 34 | 1.7 |
| 104 |  | 7 | 39 | 79 | 18 | 0.7 |
| 105 |  | 15 | 2 | 100 | 21 | 0.9 |
| 106 |  | 30 | 21 | 19 | 21 | 0.9 |

*Examples 95–100 were run for 10–16 minutes exposure at chlorine concentrations of 0.3%–3% (.05–0.5 ml) in argon. Within these ranges, higher exposure times and chlorine concentrations were used for samples with higher loadings. Examples 101–106 were conducted similarly, except that exposure times were fixed at 20 seconds for Examples 101 and 102 and at 10 minutes for Examples 103–106.

TABLE VIII

| Ex * | Si/Al | Load (%) | Conv. (%) | $S_m$ (%) | $S_t$ (%) | $S_o$ |
|---|---|---|---|---|---|---|
| 107 | 70 | 2 | 62 | 29 | 35 | 1.8 |
| 108 |  | 7 | 43 | 63 | 36 | 1.9 |
| 109 | 1220 | 2 | 54 | 28 | 34 | 1.7 |
| 110 |  | 7 | 42 | 41 | 33 | 1.7 |

*All examples were run for 20–23 minutes exposure at chlorine concentrations of 1.5% (0.2 ml) in argon. A "Blak Ray" Model B-100A UV flood lamp was used as the light source in these examples.

Table IX demonstrates the effectiveness of the invention with various 1-substituted normal alkanes. These examples were run using 10 mg samples with 2% loading on ZSM-5 zeolite (Na ZSM-5, Si/Al=24). Exposure times were 10 minutes with 0.7% (0.1 ml) chlorine in argon. In Table IX, the terminal selectivities are for the unsubstituted end or the ω position of the alkane chain. Also, the figures given for $S_m$ indicate the selectivity of the chlorination reaction for a single (one additional) substitution.

TABLE IX

| Reagent | Ex. | Conv. (%) | $S_m$ (%) | $S_t$ (%) | $S_o$ |
|---|---|---|---|---|---|
| $CH_3(CH_2)_{11}Cl$ | 111 | 27 | 52 | 43 | 5 |
|  | 112 | 27 | 53 | 41 | 5 |
| $CH_3(CH_2)_{11}Br$ | 113 | 19 | 26 | 51 | 7 |
|  | 114 | 19 | 5 | 68 | 14 |
| $CH_3(CH_2)_{10}CN$ | 115 | 14 | 57 | 60 | 10 |
| $CH_3(CH_2)_{10}C(O)H$ | 116 | 16 | 81 | 43 | 5 |
|  | 117 | 16 | 79 | 33 | 3 |
|  | 118 | 12 | 74 | 47 | 6 |

Tables X and XI show, respectively, the effect of loading and temperature on terminal selectivity in the case of a 1-substituted alkane—in particular, for dodecyl nitrile (the reagent in Example 115). The examples in Table X were run with 10 mg samples of charged ZSM-5 zeolite (Na ZSM-5, Si/Al=24). The examples in Table XI were run with 200 mg samples of the charged zeolite at 2% loading. Chlorine flow was adjusted to be 0.5 ml/min in these runs, for a concentration of 0.1% in the fluidizing nitrogen gas, but the conversion results suggest a slightly lower flow rate.

TABLE X

| Ex.* | Load (%) | Conv. (%) | $S_m$ (%) | $S_t$ (%) | $S_o$ |
|---|---|---|---|---|---|
| 119 | 2 | 12 | 67 | 60 | 10 |
| 120 | 2 | 17 | 47 | 53 | 7 |
| 121 | .5 | 15 | 47 | 50 | 7 |
| 122 | 1 | 9 | 67 | 57 | 9 |
| 123 | 4 | 5 | 80 | 30 | 3 |
| 124 | 8 | 7 | 43 | 16 | 1 |
| 125 | 2 | 46 | 61 | 56 | 8 |
| 126 | 4 | 12 | 58 | 16 | 1 |
| 127 | 8 | 6 | 50 | 6 | .4 |
| 128 | 16 | 17 | 65 | 4 | .3 |

*Chlorination:
Example 119: 10 minutes, 0.7% (0.1 ml) in argon
Examples 120–124: 10 minutes, pure chlorine (15 ml)
Examples 125–128: 20 minutes, 1.5% (0.2 ml) in with different lamp ("Blak Ray" Model B-100A UV Flood)

TABLE XI

| Temp. °C. | Ex. | Exposure (minutes) | Conv. (%) | $S_m$ (%) | $S_t$ (%) | $S_o$ |
|---|---|---|---|---|---|---|
| 25 | 129 | 5 | 10 | 50 | 56 | 9 |
|  | 129a* | 5 | 0 | — | — | — |
|  | 130 | 10 | 10 | 60 | 54 | 8 |
|  | 131 | 30 | 12 | 83 | 54 | 8 |
| 40 | 132 | 5 | 11 | 64 | 41 | 5 |
| 55 | 133 | 1 | 4 | 50 | 66 | 13 |
|  | 134 | 5 | 9 | 67 | 61 | 10 |

*UV lamp off; low level ambient light only.

Tables XII and XIII show the effects of washing the zeolite to remove excess alkane from the zeolite surface prior to exposure of the alkane charge to chlorine. Examples were run with 10 mg samples of dodecane on ZSM-5 zeolite (Na ZSM-5, Si/Al=24) and 10 minute exposure times with 0.1 ml of chlorine in argon (concentration 0.7% Cl). Table XII shows the results of examples using unwashed samples, and Table XIII shows the results of examples using washed samples. The washed samples were air dried prior to exposure to the chlorine. Mass balance analysis of the washed samples indicated residual loadings of about 2%.

TABLE XII

| Ex. | Load (%) | Conv. (%) | $S_m$ (%) | $S_t$ (%) | $S_o$ |
|---|---|---|---|---|---|
| 135 | 2 | 19 | 37 | 64 | 5.9 |
| 136 | 4 | 11 | 60 | 56 | 4.3 |
| 137 | 6 | 10 | 75 | 47 | 2.9 |
| 138 | 8 | 7 | 80 | 20 | 1.1 |
| 139 | 10 | 12 | 56 | 13 | 0.6 |
| 140 | 20 | 26 | 65 | 9 | 0.4 |
| 141 | 40 | 12 | 79 | 9 | 0.4 |

TABLE XIII

| Ex. | Load (%)* | Conv. (%) | $S_m$ (%) | $S_t$ (%) | $S_o$ |
|---|---|---|---|---|---|
| 142 | 2 | 27 | 52 | 59 | 4.7 |
| 143 | 4 | 31 | 42 | 62 | 5.4 |
| 144 | 6 | 17 | 68 | 63 | 5.7 |
| 145 | 8 | 14 | 71 | 63 | 5.7 |
| 146 | 10 | 22 | 56 | 60 | 4.9 |
| 147 | 10 | 19 | 74 | 64 | 5.9 |
| 148 | 20 | 18 | 62 | 61 | 5.3 |
| 149 | 40 | 22 | 52 | 58 | 4.6 |

*Prewashed loading

Table XIV shows the results of control experiments run using neat starting materials, duplicating reaction conditions for room temperature chlorination on zeolites as closely as possible. More particularly, a charge of alkane in pentane was placed in a reactor, and the pentane was evaporated with an argon stream. Chlorine gas (approximately 0.5 ml) was added to the reactor, and the reactor was rotated under the UV lamp for about 10 minutes.

TABLE XIV

| Compound | Conv. (%) | $S_m$ (%) | $S_t$ (%) | $S_o$ |
|---|---|---|---|---|
| n-nonane | 98 | 7 | 4 | 0.1 |
| n-dodecane | 98 | 11 | 8 | 0.3 |
| n-eicosane | 47 | 70 | 6 | 0.4 |
| 1-chlorododecane | 36 | 73 | 4 | 0.3 |
| 1-bromododecane | 95 | 27 | 3 | 0.2 |
| dodecyl nitrile | 89 | 36 | 6 | 0.4 |
| dodecanal | 59 | 53 | 5 | 0.3 |

While various specific examples of the invention have been given herein, it will be apparent to those skilled in the art that these examples are merely representative and that the invention is more generally applicable in accordance with the appended claims.

We claim as our invention:

1. A method of producing a terminally chlorinated normal alkane, at high terminal selectivity, comprising adsorbing a normal alkane into a pentasil zeolite, and chlorinating the adsorbed alkane in the zeolite.

2. The method of claim 1, wherein the Si/Al ratio of the zeolite is less than about 70 by weight.

3. The method of claim 1, wherein the Si/Al ratio of the zeolite is less than about 28 by weight.

4. The method of claim 1, wherein the zeolite is selected from the group consisting of ZSM-5 and ZSM-11 zeolites.

5. The method of claim 1, wherein the zeolite is dry and the alkane loading of the zeolite is from about 0.5% to about 8% by weight of the zeolite.

6. The method of claim 1, wherein the zeolite is wet and the alkane loading of the zeolite is from about 0.5% to about 2% by weight of the zeolite.

7. The method of claim 1, wherein the alkane is a 1-substituted normal alkane.

8. The method of claim 7, wherein the substituent of the alkane is selected from the group consisting of chlorine, bromine, nitrile, and aldehyde.

9. The method of claim 1, wherein the alkane has a chain length of from 9 to 20 carbon atoms.

10. The method of claim 1, wherein the chlorinating step is conducted at a temperature above room temperature.

11. The method of claim 10, wherein the temperature is at least about 40° C.

12. The method of claim 10, wherein the temperature is from about 40° C. to about 75° C.

13. The method of claim 10, wherein the temperature is from about 50° C. to about 60° C.

14. The method of claim 1, wherein the alkane is chlorinated with chlorine gas in pure form or diluted in an inert gas.

15. The method of claim 1, wherein chlorination of the alkane is initiated by light.

16. The method of claim 15, wherein the light is in the range of from about 2,000 to about 7,000 angstroms in wavelength.

17. The method of claim 1, further comprising washing the zeolite prior to the chlorinating step to remove excess alkane from the outer surface of the zeolite.

18. The method of claim 17, wherein the zeolite is washed with a solvent having molecules too large to enter the interior of the zeolite.

19. The method of claim 18, wherein the solvent is iso-octane.

20. The method of claim 1, wherein the chlorinating step comprises exposing a fluidized bed of the zeolite and adsorbed alkane to chlorine gas.

21. The method of claim 20, wherein the bed is simultaneously exposed to light.

22. The method of claim 21 wherein the light comprises ultraviolet light.

23. The method of claim 21, wherein the bed is simultaneously heated above room temperature.

24. The method of claim 23, wherein the bed temperature is from about 40° C. to about 75° C.

25. The method of claim 24, wherein the bed temperature is from about 50° C. to about 60° C.

26. The method of claim 1, comprising removing excess alkane from the outer surface of the zeolite prior to chlorinating the adsorbed alkane.

* * * * *